United States Patent [19]
Corn

[11] Patent Number: 5,865,808
[45] Date of Patent: *Feb. 2, 1999

[54] ANESTHESIA DOCKING STATION

[75] Inventor: Stephen B. Corn, Sharon, Mass.

[73] Assignee: Children's Medical Center Corporation, Boston, Mass.

[*] Notice: The term of this patent shall not extend beyond the expiration date of Pat. No. 5,468,230.

[21] Appl. No.: 558,179

[22] Filed: Nov. 15, 1995

Related U.S. Application Data

[63] Continuation-in-part of Ser. No. 242,031, May 12, 1994, Pat. No. 5,468,230, which is a continuation of Ser. No. 48,760, Apr. 16, 1993, abandoned.

[51] Int. Cl.[6] ................................................. A61M 5/32
[52] U.S. Cl. ........................... 604/174; 604/180; 604/248
[58] Field of Search ............................... 604/80, 81, 174, 604/180, 246, 248, 281, 282, 283, 284, 110, 164, 124, 247

[56] References Cited

U.S. PATENT DOCUMENTS

| | | | |
|---|---|---|---|
| 1,086,976 | 2/1914 | Abramovitz | 604/124 |
| 1,170,805 | 2/1916 | Eastman | 604/124 |
| 3,194,235 | 7/1965 | Cooke | 128/132 |
| 3,794,032 | 2/1974 | Derouineau | 604/248 |
| 3,957,082 | 5/1976 | Fuson et al. | 604/248 |
| 4,392,853 | 7/1983 | Muto | 604/171 |
| 4,447,236 | 5/1984 | Quinn | 604/169 |
| 4,517,971 | 5/1985 | Sorbonne | 128/133 |
| 4,561,857 | 12/1985 | Sacks | 604/174 |
| 4,578,062 | 3/1986 | Schneider | 604/174 |
| 4,582,509 | 4/1986 | Pavelka | 604/179 |
| 4,606,735 | 8/1986 | Wilder et al. | 604/180 |
| 4,633,863 | 1/1987 | Filips et al. | 128/165 |
| 4,699,613 | 10/1987 | Donawick et al. | 604/80 |
| 4,711,636 | 12/1987 | Bierman | 604/180 |
| 4,743,232 | 5/1988 | Kruger | 604/180 |
| 4,898,587 | 2/1990 | Mera | 604/174 |
| 4,941,882 | 7/1990 | Ward et al. | 604/180 |
| 4,950,230 | 8/1990 | Kendell | 604/248 |
| 4,966,590 | 10/1990 | Kalt | 604/180 |
| 4,976,698 | 12/1990 | Stokley | 604/174 |
| 5,037,398 | 8/1991 | Buchanan | 604/180 |
| 5,059,173 | 10/1991 | Sacco | 604/80 |
| 5,074,847 | 12/1991 | Greenwell et al. | 604/174 |
| 5,078,688 | 1/1992 | Lobodzinski et al. | 604/248 |
| 5,084,026 | 1/1992 | Shapiro | 604/179 |
| 5,116,324 | 5/1992 | Brierley et al. | 604/180 |
| 5,135,492 | 8/1992 | Melker et al. | 604/248 |
| 5,147,320 | 9/1992 | Reynolds et al. | 604/174 |
| 5,466,228 | 11/1995 | Evans | 604/248 |
| 5,578,013 | 11/1996 | Bierman | 604/180 |
| 5,702,371 | 12/1997 | Bierman | 604/174 |

FOREIGN PATENT DOCUMENTS

WO 94/23783  10/1994  WIPO .

*Primary Examiner*—Jerome W. Donnelly
*Assistant Examiner*—Justine R. Yu
*Attorney, Agent, or Firm*—Thomas J. Engellenner; Lahive & Cockfield, LLP

[57] ABSTRACT

A catheter docking system is provided that is easily affixed to a patient and that facilitates the secure connection of an infusion line to an anesthesia-delivering catheter. The system comprises a docking station having an adapter mounted thereon. The adapter includes a first port adapted to communicate with an infusion line and a second port adapted to communicate with an anesthesia-delivering catheter. Valve means may be provided to regulate the flow between the first and second ports. In addition, the system preferably has associated with the docking station a means for relieving any tensile strain on the catheter line.

8 Claims, 4 Drawing Sheets

ANESTHESIA DOCKING STATION

This is a continuation-in-part of U.S. patent application Ser. No. 08/242,031 filed May 12, 1994, now U.S. Pat. No. 5,468,230, issued Nov. 21, 1995, which in turn is a continuation of U.S. patent application Ser. No. 08/048,760, filed Apr. 16, 1993, now abandoned.

BACKGROUND OF THE INVENTION

The present invention relates to a device for improving connection to a patient of an anesthesia-delivering catheter and an infusion source for the anesthesia.

Epidural and continuous spinal anesthesia are common anesthetic techniques used in operating rooms, hospital wards and in pain clinics. Such anesthetic techniques also find use by outpatients in homes for the treatment of chronic pain. Anesthesia is delivered to a patient through a thin, flexible catheter, the distal end of which penetrates the patient's body to deliver the anesthesia to a desired location, usually the epidural space. The proximal end of the catheter typically is connected to an infusion line that communicates with an infusion source for delivering the anesthesia to the catheter.

Currently, anesthesia is often delivered simply by joining together the infusion line and catheter and taping the joined unit to a tongue depressor, allowing the catheter to extend over the patient's shoulder and along the patient's back to a desired insertion point. Such a connection arrangement is not satisfactory as it can often lead to catheter kinking or disconnection, possibly resulting in contamination of the epidural system and/or inadequate delivery of anesthesia. The increased use of epidural anesthesia in ambulating patients has resulted in an increased incidence of catheter disconnection, kinking and breaking, and system contamination.

Another potential hazard encountered with the use of such anesthesia delivery systems is the inadvertent injection into the epidural catheter system of substances intended for intravenous or other sites. Such errors can have life threatening consequences.

Accordingly, there is a need for a more secure and reliable anesthesia delivery system that effectively joins an infusion source to an epidural catheter system.

It is thus an object of the invention to provide a system for safely and effectively delivering spinal and epidural anesthesia. Another object is to provide a patient-mountable device that facilitates infusion line and anesthesia-delivering catheter connection. A further object is to provide such a device which increases patient comfort and mobility. It is also an object to provide a device that facilitates safe and secure connection of an infusion source to a catheter system. Other objects of the invention will be apparent from the following description of the invention.

SUMMARY OF THE INVENTION

The invention provides a device for securely joining an infusion source to an anesthesia-delivering catheter system. The device comprises a support base having an adapter mechanism mounted on a top or first surface of the support base. The adapter mechanism has at least a first port adapted to communicate with an infusion line, a second port adapted to communicate with an anesthesia-delivering catheter, and a valve means for regulating flow between the first and second ports. The device also includes a means for relieving tensile strain on the anesthesia catheter. Preferably, a bottom or second surface of the support base includes a double sided adhesive material to facilitate mounting of the device to a patient.

The device is useful in the delivery of epidural and continuous spinal anesthesia as it provides a secure connection between the infusion line and the catheter system and may also be comfortably affixed to a patient. This facilitates greater patient mobility, while at the same time reducing the risk of catheter breakage, catheter disconnection and catheter kinking. The device also enhances patient safety because the reduced risk of catheter breakage and catheter disconnection also reduces the risk of infection due to contamination of the epidural system.

Tensile strain on the anesthesia catheter can be relieved by providing an adapter line which connects between the second port and the proximal end of the anesthesia-delivering catheter. The adapter line preferably is a stretchable or expandable conduit having sufficient inner diameter to accommodate fluid flow. Preferably, the adapter line is a stretchable line having a coiled region. In an alternative embodiment a stretchable, coiled region can be incorporated directly into the catheter line.

Tensile strain on the catheter may also be reduced without connecting a stretchable adapter line between the second port and the catheter. In such an embodiment the proximal end of the catheter can be connected directly to the second port. Further, a length of a proximal portion of the catheter is engaged by flanges or stanchions mounted on opposite ends of the top support base. In this way, slack can be created in the catheter line to relieve any tensile strain. Alternatively, a zone can be formed on the surface of the support base to engage a portion of a proximal length of the catheter to create slack in the catheter line.

In another embodiment the device further includes a third port in fluid communication with the first and second ports. The third port facilitates the delivery of medicaments (e.g., anesthetics) to the anesthesia-delivering catheter.

DETAILED DESCRIPTION OF THE DRAWINGS

Figure 1:
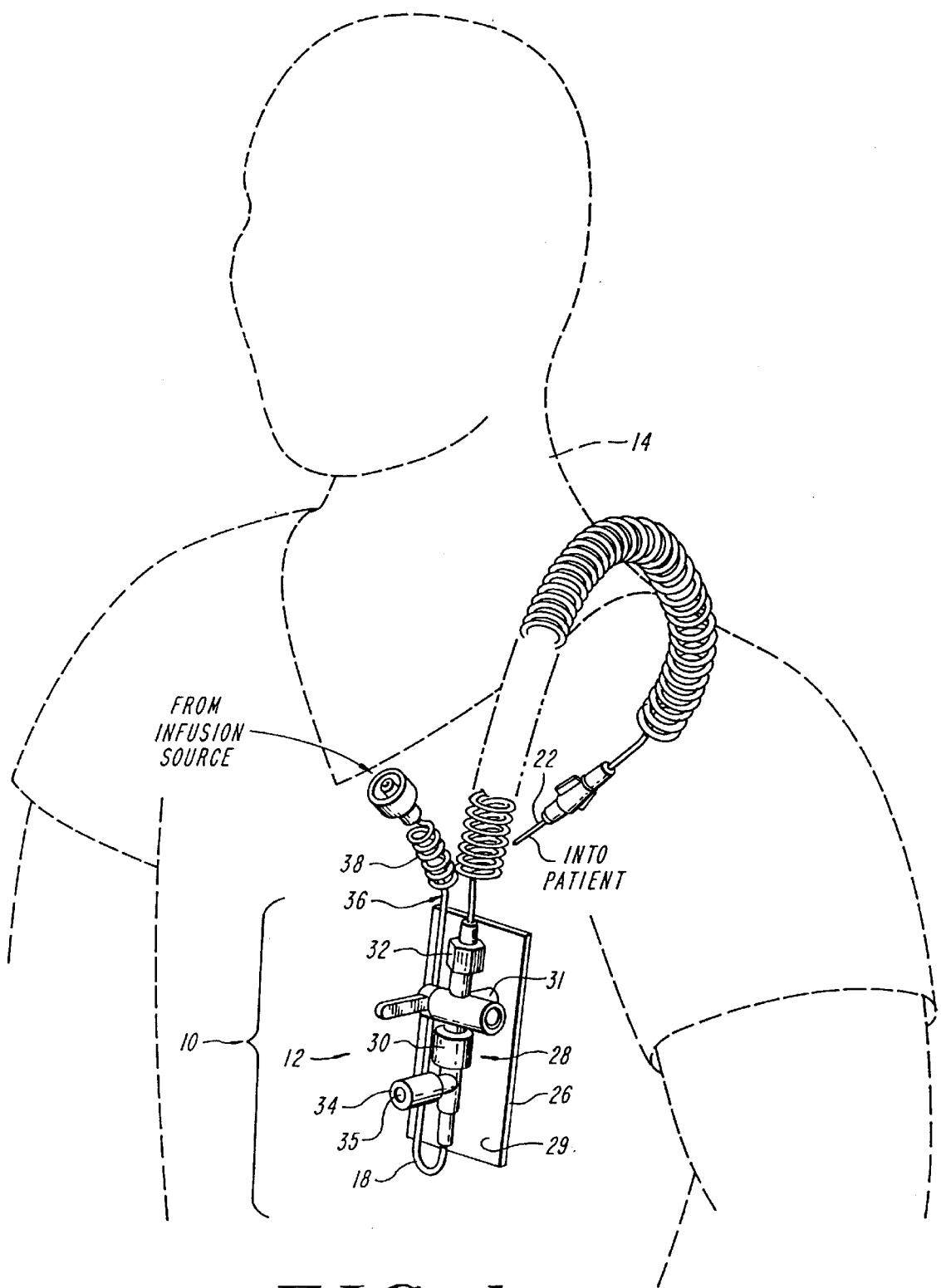
FIG. 1 is a perspective view illustrating an anesthesia docking station of the present invention while in use by a patient.

As shown in FIG. 1, anesthesia docking system 10 of the invention comprises a docking station 12 that can be affixed to a patient 14. The system 10 comprises an infusion source (not shown) communicated through an infusion line 18 to the docking station 12. The infused fluid, such as an anesthesia-containing fluid, is communicated to a catheter line 22, the distal end of which delivers anesthesia to the epidural or the subarachnoid space of the patient. The system is best adapted for use in the delivery of epidural anesthesia and continuous spinal anesthesia.

Figure 2:
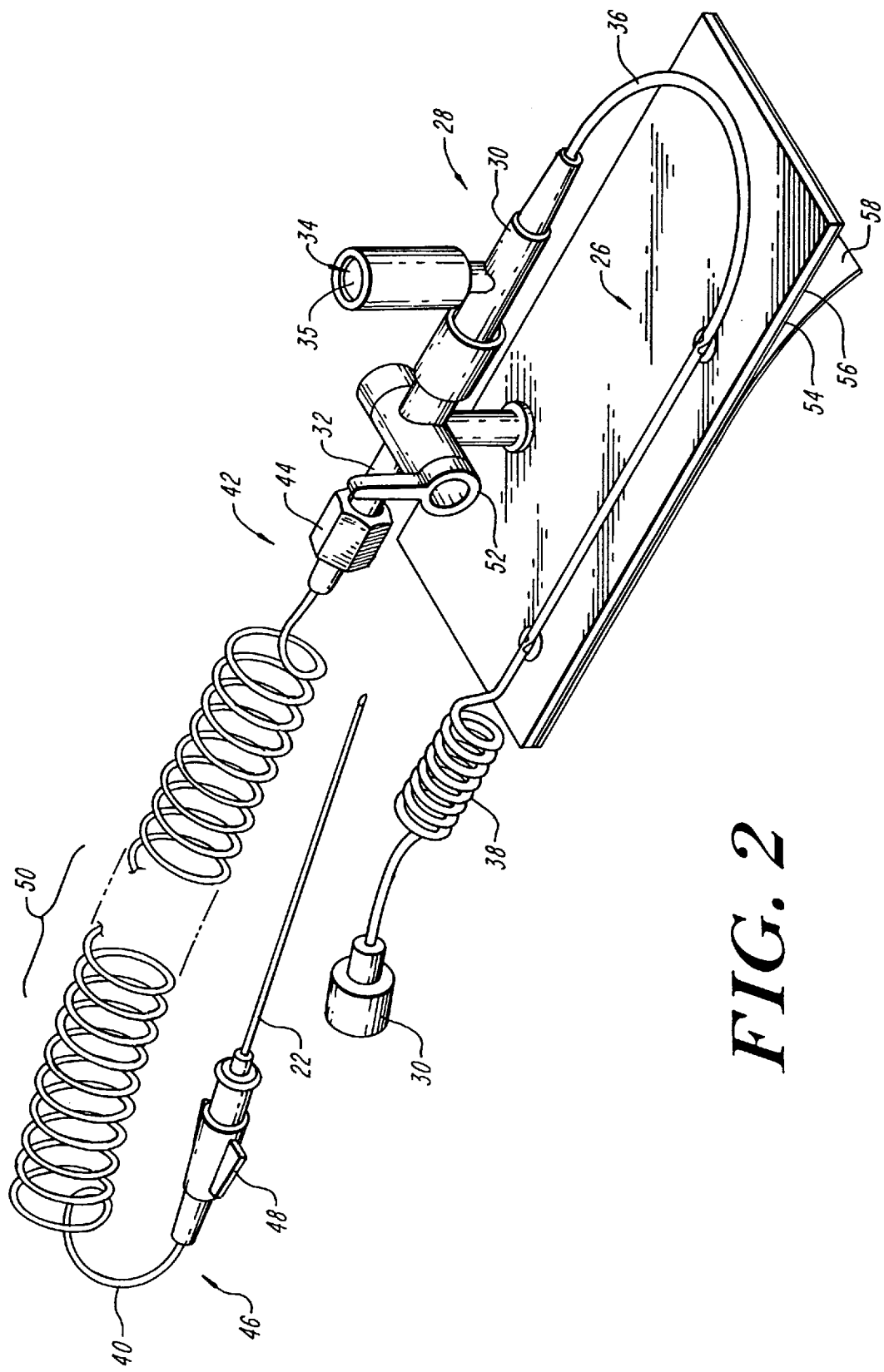
FIG. 2 is a perspective view of the anesthesia docking station shown in FIG. 1.

Referring to FIGS. 1 and 2, docking station 12 comprises a support base 26 having mounted thereon an adapter mechanism 28. Preferably, the adapter mechanism 28 is mounted upon a flange 31 such that it is positioned above the surface 29 of support base 26. The adapter mechanism 28 includes a first port 30 adapted to communicate with infusion line 18 and a second a port 32 adapted to communicate with catheter 22. A third port 34 (shown in FIG. 2) may also be mounted on the adapter mechanism 28, intermediate first port 30 and second port 32. Third port 34 can be used to deliver medicament to the catheter line 22. Ideally, port 34 includes at a top portion thereof a self-closing seal 35.

As illustrated in FIG. 2, the first port 30 may be mounted on a flexible fluid communication line 36 that extends between port 30 and the adapter mechanism 28. Preferably, at least a portion of line 36 includes a coiled region 38 that enables extension of the line 36. Alternatively, port 30 can be mounted directly on adapter mechanism 28 as shown in FIG. 3.

Figure 3:
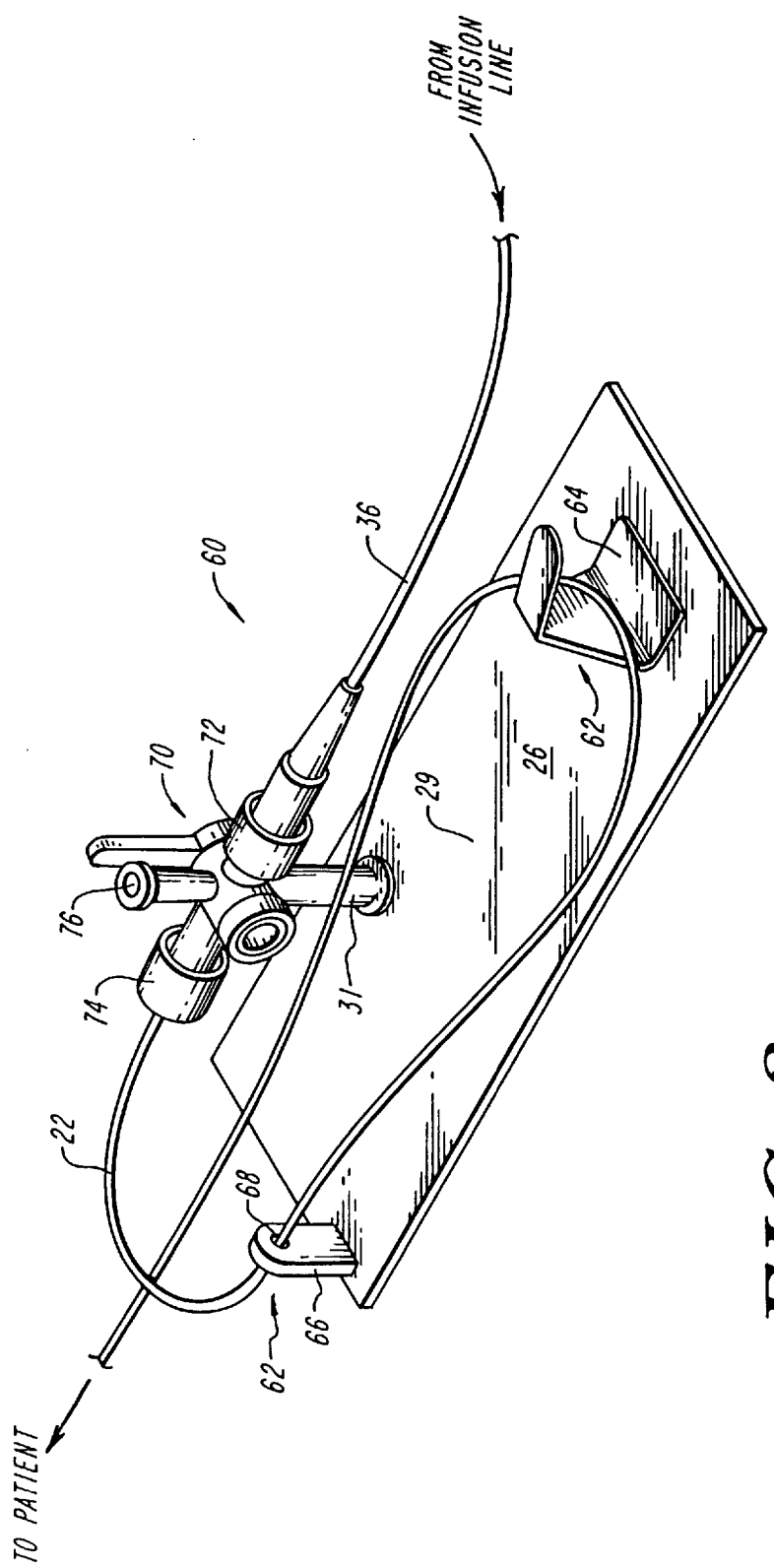
FIG. 3 is an alternative anesthesia docking station useful with the present invention.

The proximal end of catheter 22 can be connected directly to second port 32 as illustrated in FIG. 3. Alternatively, as illustrated in FIG. 2, the proximal end of catheter 22 can be connected to port 32 through a catheter adapter line 40. Catheter adapter line 40 has a proximal end 42 with a connector 44, such as a luer lock, friction fit connector, or threaded connector, for mounting to port 32. The distal end 46 of catheter adapter line 40 includes a standard connector 48 for mounting to catheter 22. Catheter adapter line adapter 40 preferably is manufactured from a medically compatible polymeric material and has an inner diameter sufficient to accommodate fluid flow. Catheter adapter line 40 preferably includes a coiled region 50 that enables extension of line 40 and movement of catheter 22 without placing undue tensile strain on either catheter line 40 or catheter line 22. The length of catheter adapter line 40 may vary depending upon requirements of a given application. Generally, however, the line is approximately 16 inches in length and coiled region 50 enables catheter adapter line 40 to be extended to at least 3 to 5 times its normal length.

Figure 4:
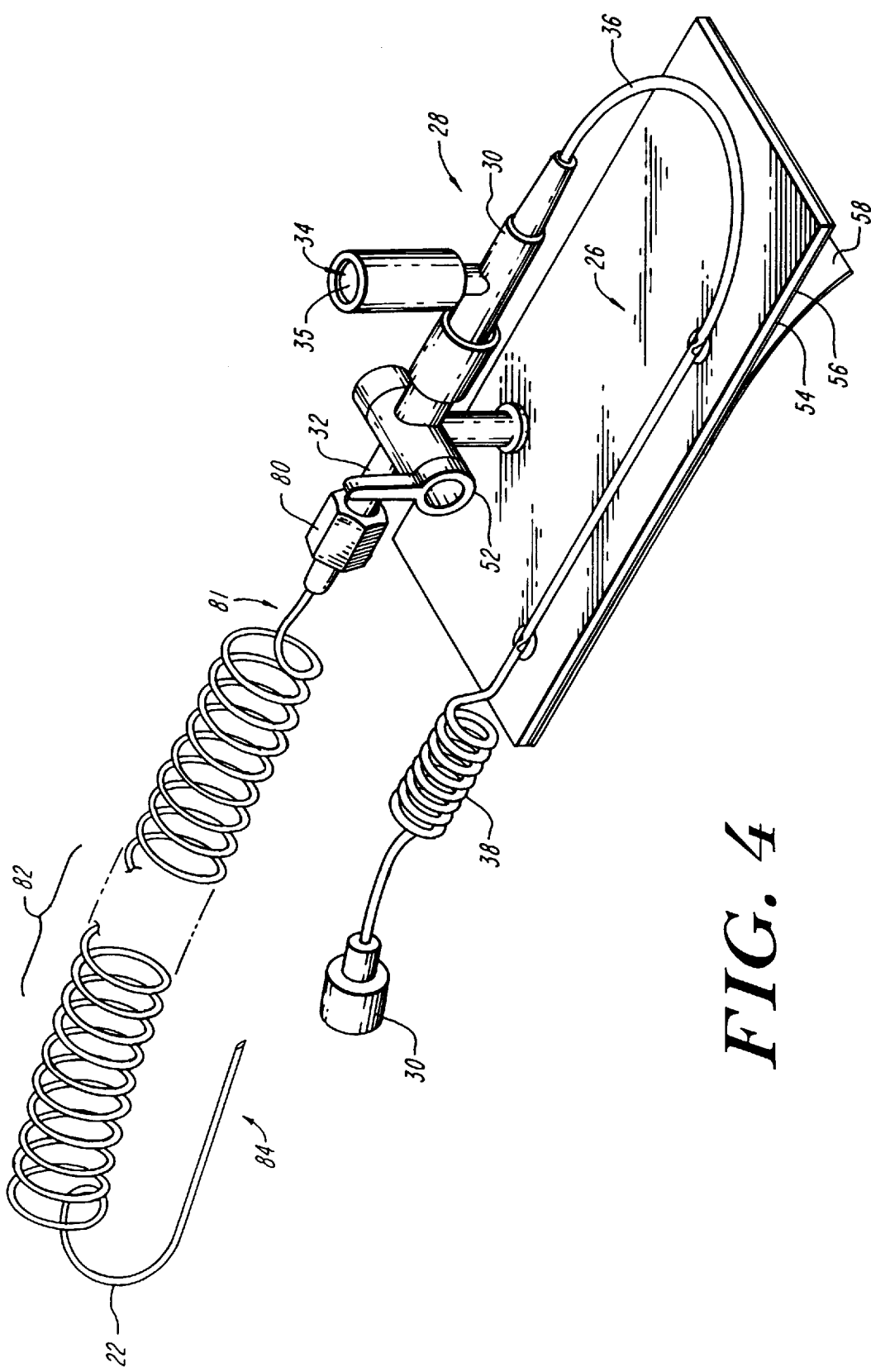
FIG. 4 is a perspective view of the anesthesia docking station of FIG. 1 incorporating an extensible element directly into the catheter line.

Similarly, as shown in FIG. 4, the means for relieving tensile strain on the anesthesia catheter may be incorporated within the catheter itself.

According to this embodiment, the support base 26 and adapter mechanism 28 illustrated in the anesthesia docking system 10 shown in FIG. 4 are substantially the same as described above with respect to FIGS. 1 and 2. As illustrated, a proximal end 81 of catheter line 22 communicates within the adapter mechanism 28 through a connector 80. The distal end 84 of the catheter line is adapted to be placed within a patient's body.

An extensible means or element 82 is formed in the catheter line 22 intermediate the proximal and distal ends 81, 84 of the catheter. The extensible element 82 can be in the form of a region of flexible, coiled or helically wound catheter line. The presence of extensible element 82 within the catheter line 22 enables intermediate and proximal portions of the catheter to be subjected to tensile strain without causing the distal end 84 to be subjected to such strain. This feature can provide more secure fixation of a catheter within a patient's body, thus resulting in a lower incidence of catheter disconnects.

The adapter mechanism 28 preferably includes a valve 52, such as a stopcock, infusion port, or a similar device, to regulate fluid flow between the first and third ports and the second port.

Support base 26 is a rigid or flexible member having a shape and dimensions suitable to its intended application. This support member may, for example, be rectangular, oval or circular in shape. A suitable rectangular base 26 can have dimensions of about 1 ½×3 ½ inches. One having ordinary skill in the art will appreciate that the dimensions of the support base may be modified as necessary. A bottom surface 54 of support base 26 preferably includes an adhesive material or other means of mounting the support base to the skin of a patient. Preferably, a cushioned, two-sided adhesive 56 is placed on the bottom surface 54 of support base 26. A removable release sheet 58 preferably protects the adhesive surface of the adhesive layer 56 before use.

FIG. 3 illustrates docking station 60, forming an alternative embodiment of the invention. As illustrated, adapter mechanism 70 is secured by way of mounting flange 31 to a top surface 29 of support base 26. The adapter mechanism includes a first port 72, second port 74 and third port 76. The three ports mounted upon the adapter mechanism 70 in alternative docking station 60 serve the same purpose as the corresponding ports in docking station 12. However, port 72 communicates directly with catheter line 22. Docking station 60 also includes two stanchions 62 mounted on opposite ends of docking station 60. Stanchions 62 are adapted to engage a proximal portion of catheter line 22 to provide slack in the catheter line and thus relieve any tensile strain on the catheter line 22. In one embodiment, one stanchion may comprise a U-shaped flange 64 while the other comprises a vertical member 66 having a central aperture 68 disposed therein. As illustrated, the catheter may engage flange 64 and be threaded through aperture 68 of member 66 before being directed to a desired location on a patients body. The threading of the catheter line through aperture 68 enables a desired amount of slack to be created in catheter line 22.

The docking system of the present invention is advantageous as it is able to be comfortably and securely affixed to a patient. At the same time, the infusion line may be securely joined with a catheter line to deliver an anesthetic to a patient. The connection of the infusion line and the catheter line typically utilizes well known, reliable locking mechanisms such as luer locks, friction fit connectors, or threaded connectors, and thus virtually eliminates any risk of unintended disconnection of the catheter line from the infusion source. The docking station also provides a surface which can be clearly marked to indicate the intended use of the various ports to facilitate rapid and easy assembly. Moreover, due to the secure attachment of the docking station to the patient and the secure connection between the infusion source and the catheter line, ambulatory patients in need of pain control treatments have greater freedom of movement.

Various modifications may be made in the device described above without departing from the intended scope of the invention.

What is claimed is:

1. A device for anchoring an infusion line and a drug delivering catheter to a patient comprising:

a support base having first and second oppositely facing surfaces;

means for affixing the support base to a patient with the second surface in contact with the patient;

an adapter mechanism mounted upon the support base, the adapter mechanism having at least a first port and a second port in fluid communication with each other, the first port being adapted to receive an infusion line; and a drug-delivery catheter attached by way of a connector to the second port, the canther comprising a catheter line, said catheter line including an extensible means for relieving tensile strain on the catheter between the second port and a distal end of the catheter.

2. The device of claim 1 further comprising second extensible means disposed between the first port and an infusion line for relieving tensile strain on the infusion line.

3. The device of claim 1 wherein the support base comprises at least one flexible base member.

4. The device of claim 1 wherein the first port connects to the infusion line by way of a connector selected from the group consisting of a luer lock, friction fit, and threaded connectors.

5. The device of claim 1 wherein the second port is adapted to be connected to the drug-delivering catheter by way of a connector selected from a group of a luer lock, friction fit, and threaded connectors.

6. The device of claim 1 wherein the adapter mechanism further comprises a third port and fluid communication with the first and second ports, the third port being adapted facilitate the delivery of medicaments to the drug delivered catheter.

7. The device of claim 1 wherein the device further comprises a valve means for regulating the fluid flow between said first and second ports.

8. The device of claim 1 wherein the extensible means for relieving tensile strain on the catheter comprises a coiled, stretchable region disposed between the second port and a distal end of the catheter.

* * * * *